(12) United States Patent
Lary et al.

(10) Patent No.: US 8,551,129 B2
(45) Date of Patent: Oct. 8, 2013

(54) TREATMENT OF CORONARY STENOSIS

(76) Inventors: Todd P. Lary, Homestead, FL (US); Banning G. Lary, Miami, FL (US)

(*) Notice: Subject to any disclaimer, the term of this patent is extended or adjusted under 35 U.S.C. 154(b) by 746 days.

(21) Appl. No.: 12/270,889

(22) Filed: Nov. 14, 2008

(65) Prior Publication Data

US 2009/0125044 A1 May 14, 2009

Related U.S. Application Data

(60) Provisional application No. 60/987,793, filed on Nov. 14, 2007.

(51) Int. Cl.
*A61B 17/3207* (2006.01)
(52) U.S. Cl.
USPC .......................................................... 606/159
(58) Field of Classification Search
USPC ......... 606/159, 167, 170, 174, 191, 192, 198; 604/22, 104, 105, 106, 107, 108, 109; 600/562, 564, 570; 227/180.1
See application file for complete search history.

(56) References Cited

U.S. PATENT DOCUMENTS

| | | | | |
|---|---|---|---|---|
| 4,585,000 A * | 4/1986 | Hershenson | ................... | 606/194 |
| 4,721,103 A * | 1/1988 | Freedland | ...................... | 606/319 |
| 5,053,044 A * | 10/1991 | Mueller et al. | ................. | 606/159 |
| 5,196,024 A * | 3/1993 | Barath | .......................... | 606/159 |
| 5,713,913 A | 2/1998 | Lary | | |
| 5,904,679 A * | 5/1999 | Clayman | .......................... | 606/39 |
| 6,081,738 A * | 6/2000 | Hinohara et al. | ............. | 600/407 |
| 6,716,230 B2 * | 4/2004 | Whitman | ....................... | 606/198 |
| 2005/0222596 A1 * | 10/2005 | Maschke | ........................ | 606/159 |
| 2006/0235334 A1 * | 10/2006 | Corvi et al. | .................... | 600/564 |

* cited by examiner

*Primary Examiner* — Ryan Severson
*Assistant Examiner* — Rachel S Papeika
(74) *Attorney, Agent, or Firm* — Daniel S. Coolidge

(57) ABSTRACT

The invention describes includes a device and method for dilating a coronary arterial stenosis and for creating a transection in the myocardium. The transection creates a new artery composed partially of the old artery and partially of the normal healing tissue and myocardium. Several dilating means are described, as well as several cutting means and alignment means by which the cutting means may be located and properly oriented. In operation, the dilating means, cutting means and alignment means are advanced in the distal end of a catheter, which may be guided into position by a guidewire.

3 Claims, 18 Drawing Sheets

TREATMENT OF CORONARY STENOSIS

PRIORITY

This application claims priority from U.S. Provisional Application 60987793 filed Nov. 14, 2007, and is incorporated herein by reference.

TECHNICAL FIELD

The present invention relates generally to coronary artery surgery and is directed particularly to an improved device for the surgical treatment of stenotic or occluded major coronary vessels while the heart is beating and without the use of the heart-lung machine.

BACKGROUND INFORMATION

In recent years occlusive coronary artery disease has been surgically treated with the use of various artery by-pass techniques involving cardiopulmonary by-pass. Although these techniques have been highly successful and can be performed with minimal risk, the unusual surgical skill required, and the complexity of the procedure, limits the operation to a small percentage of those patients who could otherwise be benefited.

In attempts to surgically treat the vast number of coronary artery disease patients to whom the usual open-heart coronary artery by-pass operation was not available or otherwise not indicated, various surgical techniques have heretofore been devised to effect myo-cardial revascularization and neo-vascularization. These procedures can be performed on the beating heart without cardiopulmonary by-pass, thereby greatly simplifying the procedure with an attendant lessening of the risk. These new techniques, moreover, have been greatly advanced by the comparatively recent development of cine-coronary arteriography.

Most promising of the new surgical techniques has been the direct approach to increase the diameter of the coronary arteries narrowed or obstructed by the disease. One technique involves longitudinal incision of the myo-cardial side of the coronary artery at the site of the stenosis or occlusion, with the insertion of a scalpel through a small incision made in the wall of the coronary artery distal to the occlusion. This procedure effects an immediate increase in the size of the lumen for restored blood flow, but in the calcific rigid artery the lumen may remain small. Upon healing, the inside myo-cardial tissue assumes an intima-like surface defining, with the contiguous decompressed arterial zone, a new lumen having an approximately normal diameter. In another of the new surgical techniques, known as percutaneous translumenal coronary angioplasty, an inflatable balloon carried at the end of a catheter or the like is passed through the affected artery to the site of the stenosis as observed in cine-coronary arteriography, and then inflated to compact the stenonic plaque and thereby increase the lumen size by dilation. A distinct advantage of this technique is that the catheter can be inserted through a peripheral artery, thereby obviating surgical opening of the chest wall to expose the heart. This technique, however, has limited application because of major problems in its use in the treatment of stenoses associated with coronary artery rigidity, obstruction, and with single severe and multiple stenoses.

Over the years, the blockage of human arteries has become a leading medical concern. This is so because a variety of serious medical complications may result from arterial blockages that reduce blood flow through an affected artery. More specifically, an arterial blockage may result in damage to the tissue that relies on the artery for its blood supply. For example, if a blockage occurs in an artery leading to the brain, a stroke may result. Similarly, if a blockage occurs in an artery which supplies blood to the heart, a heart attack may result.

Typically, arterial blockages are caused by the build-up of atherosclerotic plaque on the inside wall of the artery. These blockages, which are commonly called stenoses, may result in a partial, or even complete, blockage of the artery. As a result of the dangers associated with these arterial blockages, a variety of procedures have been developed to treat them. An angioplasty procedure is, perhaps, the most commonly used procedure for such treatment. An angioplasty procedure involves the use of an inflatable angioplasty balloon to dilate the blocked artery. A typical inflatable angioplasty device, for example, is disclosed in U.S. Pat. No. 4,896,669 which issued to Bhate et al. The Bhate et al. angioplasty device includes an inflatable angioplasty balloon which is insertable into a peripheral artery of a patient for positioning across a stenosis. Once positioned, the angioplasty balloon is then inflated to dilate the stenosis within the artery thereby improving the blood flow through the artery.

While angioplasty balloons have been widely accepted for the treatment of stenoses, recent studies have indicated that the efficacy of the dilation of a stenosis is enhanced by first, or simultaneously, incising the material that is creating the stenosis. Not surprisingly then, angioplasty balloons have been equipped with cutting edges, or atherotomes. These cutting edges are intended to incise the stenosis during the angioplasty procedure to facilitate dilation of the stenosis.

An example of an angioplasty balloon equipped with cutting edges is disclosed in U.S. Pat. No. 5,196,024 which issued to Barath for invention entitled "BALLOON CATHETER WITH CUTTING EDGE." The Barath device includes an inflatable angioplasty balloon with a number of atherotomes mounted longitudinally on its surface. During the inflation of the Barath balloon, the atherotomes induce a series of longitudinal cuts into the stenotic material as the balloon expands to dilate the stenosis. As a result of such longitudinal cuts, the stenosis is more easily dilated, and the likelihood of damaging the artery during dilation is significantly reduced.

In general, the use of angioplasty has been found to be an effective means for reducing arterial blockage associated with the buildup of atherosclerotic plaque. In some cases, however, it has been found that the atherosclerotic plaque which forms a particular stenotic segment may be too rigid to be effectively dilated. In such cases, traditional angioplasty techniques have been found to be largely ineffective and, in some cases, even harmful. As a result, a number of differing techniques have been developed for the treatment of hardened, or rigid stenotic segments.

One such technique, which is specifically targeted at the coronary arteries, is transection. Transection, as applied to the coronary arteries, involves the creation of an elongated incision within the artery where the targeted stenosis is located. More specifically, a longitudinally oriented incision is created which spans the targeted stenosis and is positioned along the wall of the artery which is closest to the cardiac muscle. Creation of the incision causes the formation of a new arterial segment, with the new segment being composed partially of the previously occluded artery, and partially of the heart muscle, or myocardium. The new arterial segment is created from the natural healing process that to create a coronary-myocardial artery. Effectively then, transection overcomes the occluding effect of atherosclerotic plaque by allowing the occluded artery to expand into the heart muscle or myocardium. A description of this procedure is provided in "Coronary Artery Incision and Dilation" Archives of Surgery, December 1980, Volume 115, Pages 1478-1480, by Banning Gray Lary, M.D.

For the transection procedure to succeed, it is important that the incision be made on the portion of the coronary artery which directly faces the heart muscle. This is so because the transection procedure involves cutting through the arterial wall, a procedure which would ordinarily result in an uncontrolled blood loss and, perhaps, the death of the patient. However, if the transection is made on the portion of the artery against the heart, the epicardial tissues which cover the heart and the coronary arteries prevent the loss of blood, allowing the new artery to form.

Unfortunately, in the context of a transection procedure, currently available angioplasty balloons have a particular disadvantage. More specifically, practice has shown that it is generally difficult to direct the atherotomes of a traditional angioplasty balloon with the accuracy required for a successful transection. Instead, when a traditional angioplasty balloon is employed, there is an ever present danger that the transection will be created in a part of the arterial wall that is not adjacent to the heart. Specifically, there is a present inability to precisely control the position an angioplasty balloon and cutting edge in both a longitudinal and a rotational direction.

Another disadvantage associated with the use of traditional angioplasty balloons for the creation of coronary transections involves the depth of the created incision. More specifically, practice has demonstrated that effective transection requires that the created incision be deep enough to allow the new artery to form.

Another problem associated with traditional balloon angioplasty is that when inflated, perfusion is interrupted. This limits the time during which the incision may be made.

BRIEF SUMMARY

The present invention describes a device and a means for dilating a coronary stenosis, aligning a cutting means, and incising the coronary stenosis proximate the heart. They can be placed within a catheter for placement at the stenosis. Embodiments of the dilating means include a traditional angioplasty balloon, an expanding bands or "chef's hat" technique, and expanding sides of a containing catheter technique. Cutting means embodiments include a spiral knife, a scissors jack operated blade, an RF cutting wire means and a sliding retractable blade.

Alignment means embodiments include magnetic field emitters and sensors. One embodiment includes a magnet placed on the distal end of the catheter and a external magnetic sensor capable of detecting the orientation of the magnet. Alternatively, a magnetic sensor may be placed at the distal end of the catheter and a magnetic field applied externally.

Other embodiments of the alignment means include a photo-detector placed on the distal end of the catheter and an external light source. Yet another embodiment includes a sensor to detect the electrical signals of the heart, at the distal end of the catheter so as to give maximal signal when closest to the heart, and in relationship to the cutting means to enable positioning.

Yet another embodiment of a positioning means uses a transmitter and receiver. Either may be placed on the catheter and the other externally. Yet another embodiment uses an x-ray opaque device placed at the distal end of the catheter the sensing of which by an external x-ray emitter support allows positioning.

The present invention relates generally to endovascular devices that are used to increase the lumen of a restricted vessel of the body. Moreover it pertains specifically to cutting and dilating catheters used to incise a coronary artery through its vessel wall and further into the myocardium to allow for the dilation and opening of that restricted area.

Moreover it pertains specifically to endovascular devices that can be positioned to cut in a known direction and known orientation. It pertains to an apparatus that will allow the incision of the stenosis and dilation of the vessel from the periphery, i.e. the leg or neck away from the stenotic section.

BRIEF DESCRIPTION OF THE DRAWINGS

These and other features and advantages of the present invention will be better understood by reading the following detailed description, taken together with the drawings wherein:

FIG. 4C shows the dilation assembly without surrounding structures for greater clarity.

Like reference numbers and designations in the various drawings indicate like elements.

DETAILED DESCRIPTION

In view of the limitations now present in the prior art, the present invention provides new and useful features and mechanisms for the incision of the coronary artery and myocardium. The present invention utilizes an alignment means to properly position a cutting means, a cutting means to perform cutting of the coronary artery and myocardium, a dilating means to expand the vessel and a perfusing means to supply blood to the distal portion of the vessel.

The alignment means, cutting means, and perfusing means are contained in an endovascular catheter(s). Preferably, the catheter is formed with a guidewire lumen which extends the=rough the length of the catheter and through which a guidewire may be run. The guidewire may be chosen from a variety of medical guidewire types well known in the art.

When properly placed into position from the periphery, these embodiments, in coordination with one another, are used to reconfigure the blood vessel to a desired new geometry. Once the reconfiguration is completed the catheter is then retracted and the entry wound sealed.

Figure 1A:
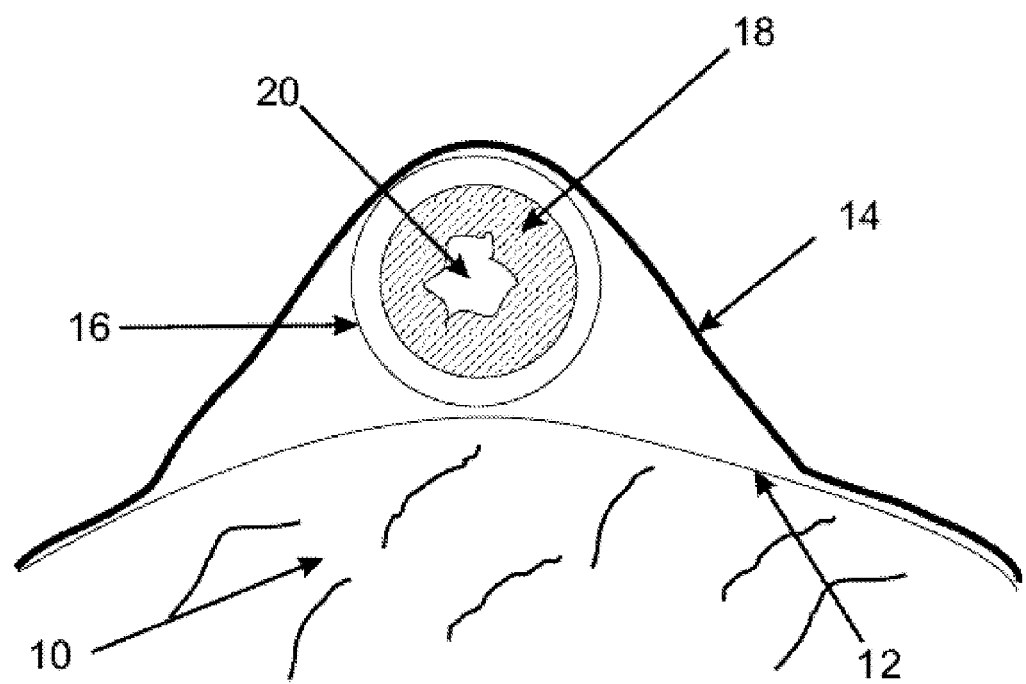
FIGS. 1A and 1B show respectively a transected coronary artery before and after treatment.
Figure 1B:
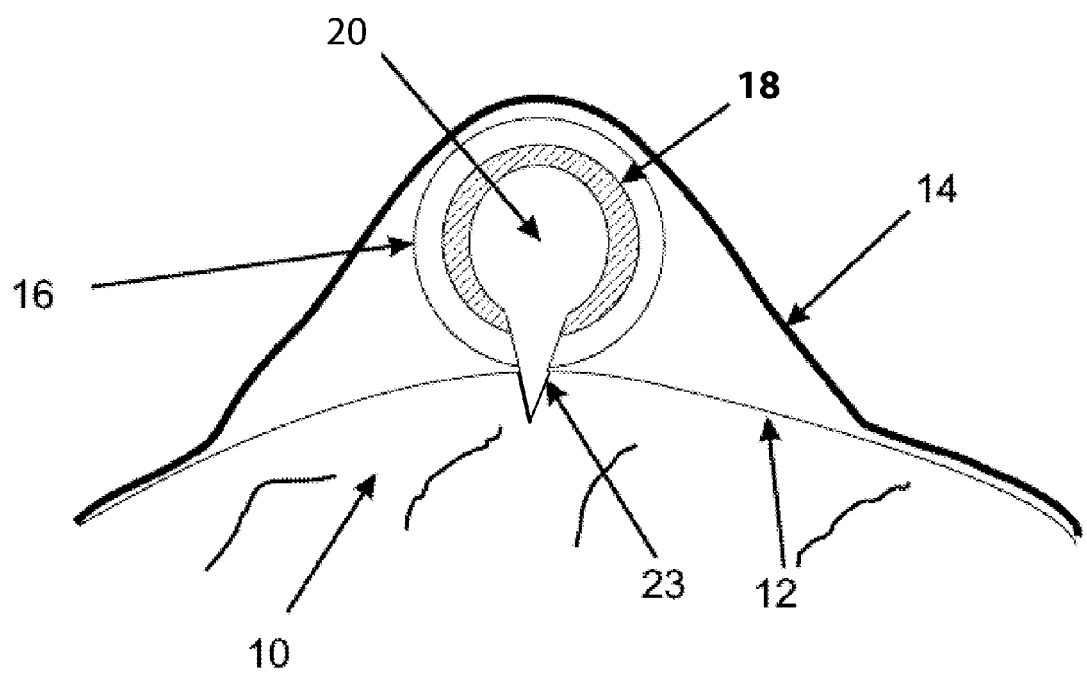

Referring to FIG. 1B, the same artery 16 is shown after coronary artery incision and dilation. The stenosis 18 has been expanded, leaving a larger lumen 20. The surface of the myocardium 12 has been incised 23 and the cut has advanced into the myocardium 10, heart muscle itself.

Dilation may be performed by a traditional angioplasty balloon, with the attendant stoppage of perfusion noted. In such case, the balloon may be inflated by means well known in the art.

One or more expanders 30 can beneficially be utilized. They need not surround the circumference of the catheter 28, but rather can be utilized in conjunction with co-located cutting means. An advantage of the chef's hat technique is that perfusion can continue in the interstices between the expanders when expanded.

Figure 2A:
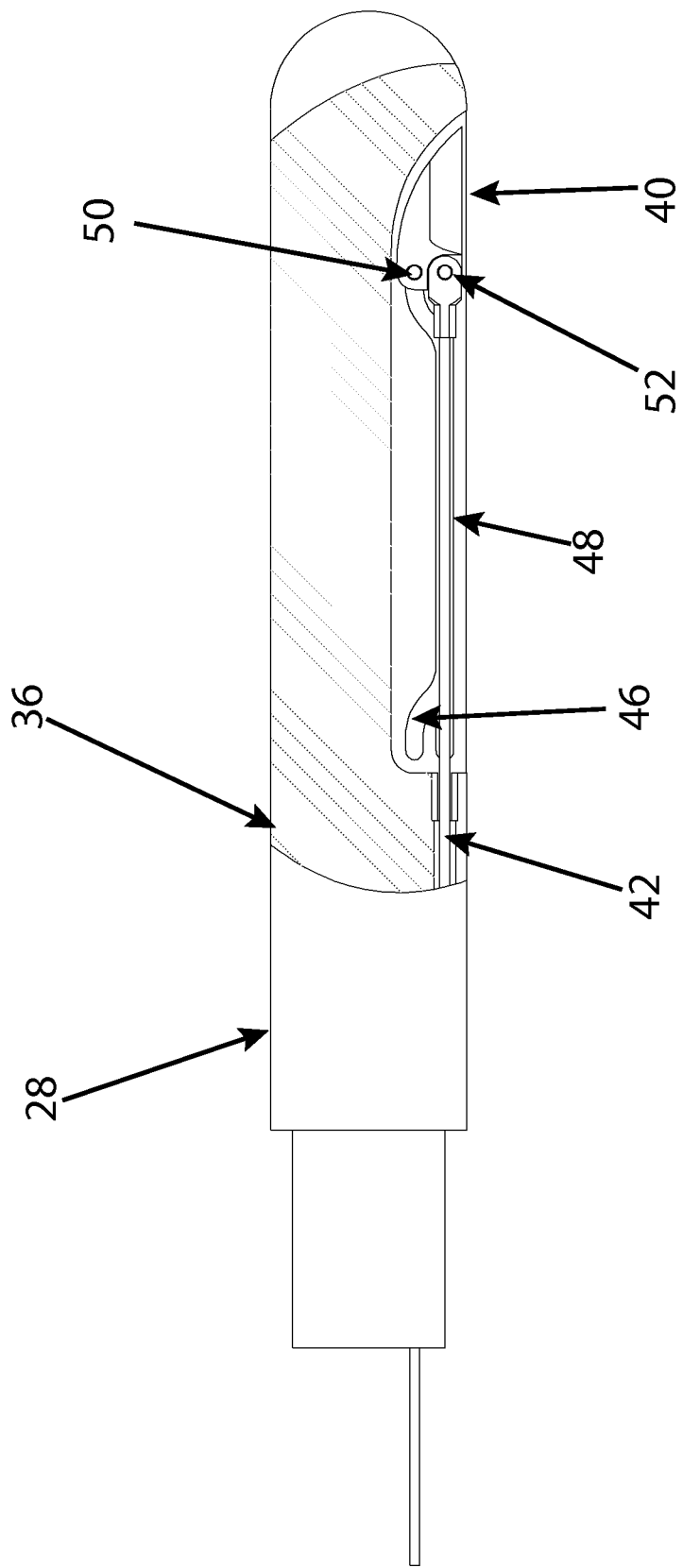
FIGS. 2A and 2B show a slidable retractable knife.
Figure 2B:
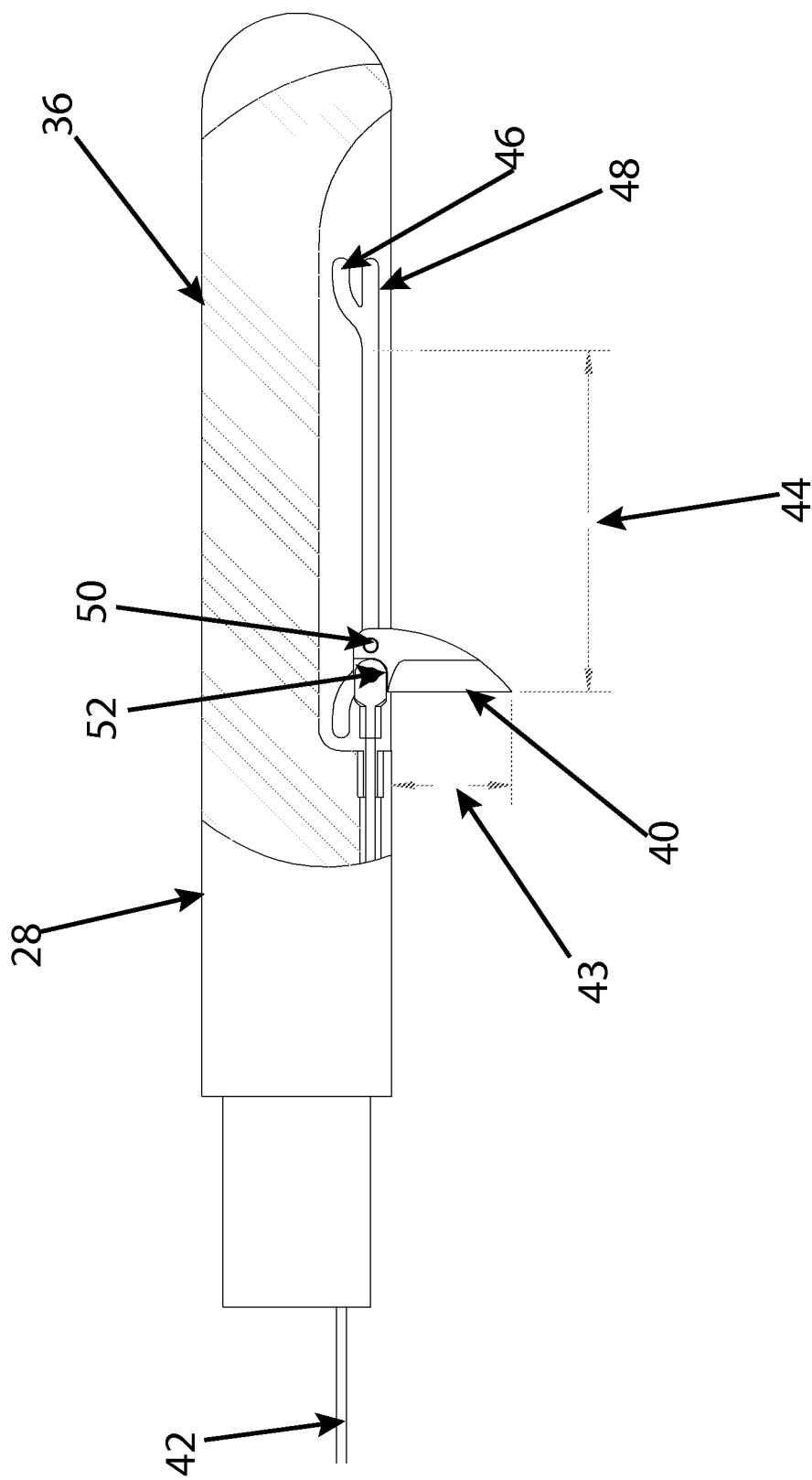

For example, FIG. 2A shows a cutaway view 36 of a sliding retractable knife. The sliding retractable knife comprises a blade controllable by a control wire 42 running through the catheter 28 to the proximal end not shown) of the catheter 28. In FIG. 2A, the blade 40 is shown refracted and attached to a control wire 42. When the control wire 42 is pulled toward the proximal end of the catheter 28, as shown in FIG. 2B, the blade 40 extends through a slot 100 (seen in FIG. 7) to a depth 43 and moves relative to the catheter 28 an incision length 44.

Figure 3A:
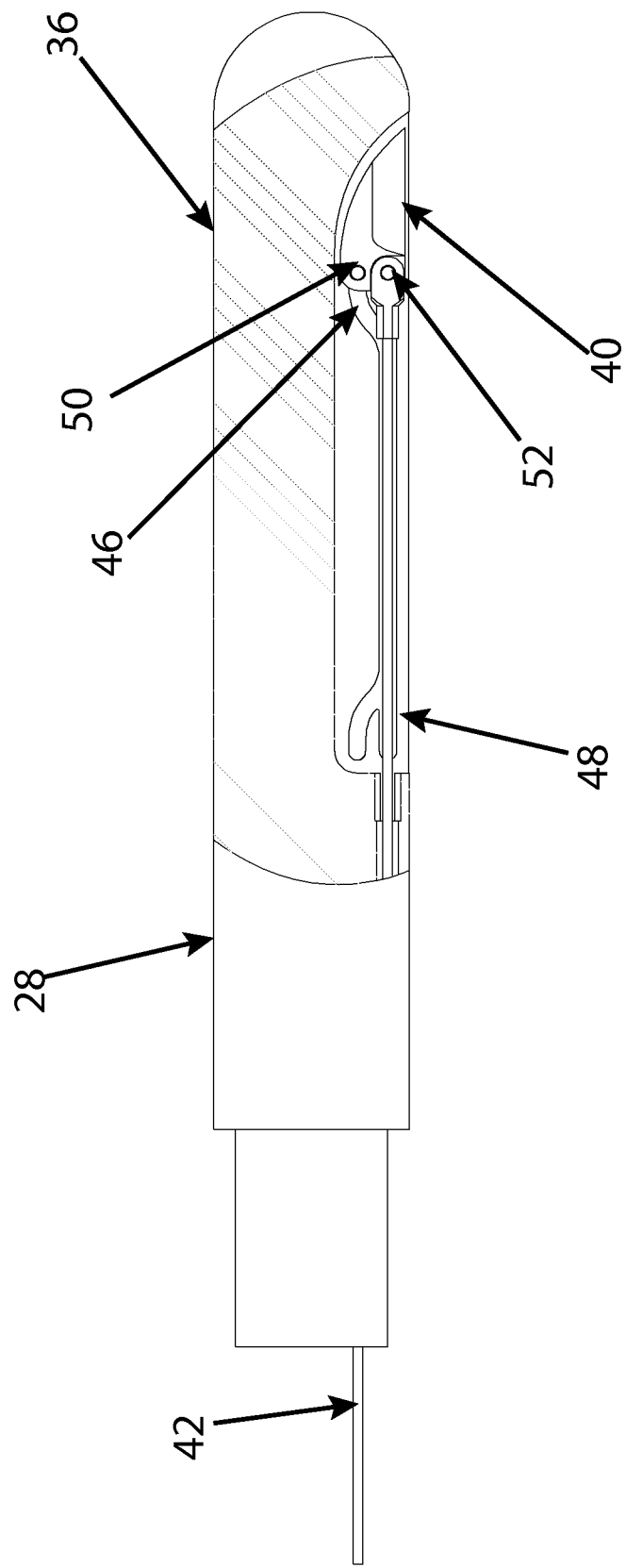
FIGS. 3A, 3B, 3C and 3D show successive views of a sliding retractable knife.

The operation of the sliding retractable knife may be seen more clearly in FIGS. 3A through 3D which show a cutaway view of a portion of the catheter 28 containing the sliding retractable blade 40. In FIG. 3A, the blade 40 is shown fully refracted. An upper control slot 46 and a lower control slot 48 are shown. In operation, there would be one upper and one lower control slot in rails on each side of the catheter 28. (The second control slots are not visible in the cutaway view.) The blade 40 has an upper control pin 50 fitted into the upper control slot 46, and likewise a lower control pin 52 fitted into the lower control slot 48.

Figure 3B:
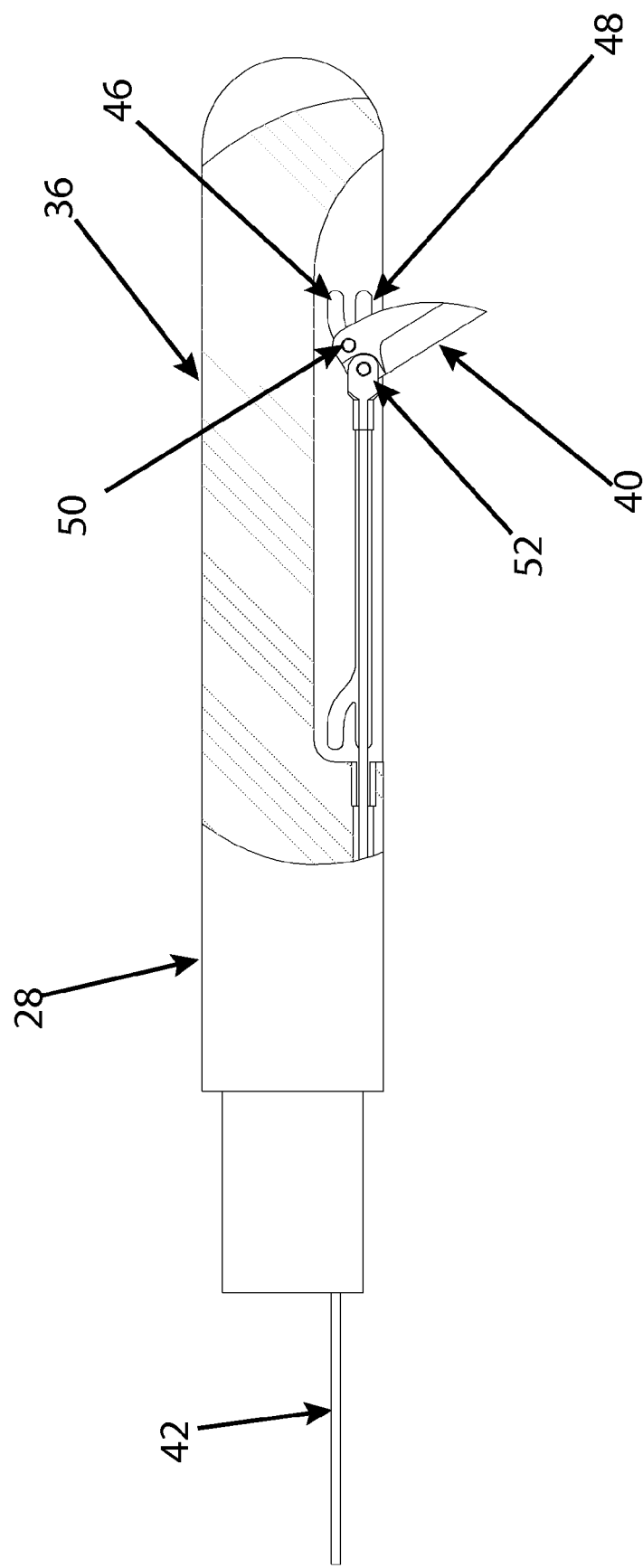
Figure 3C:
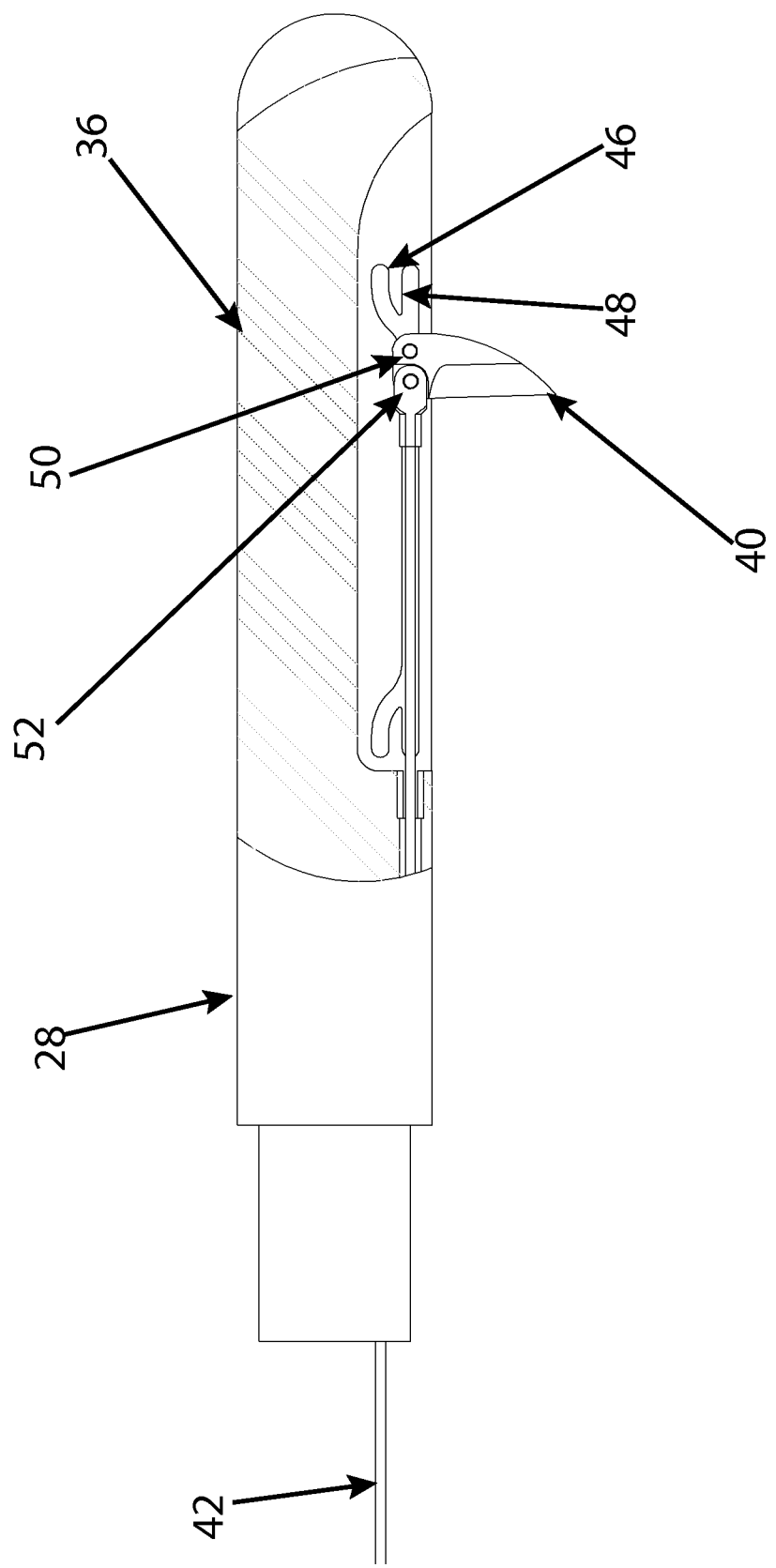
Figure 3D:
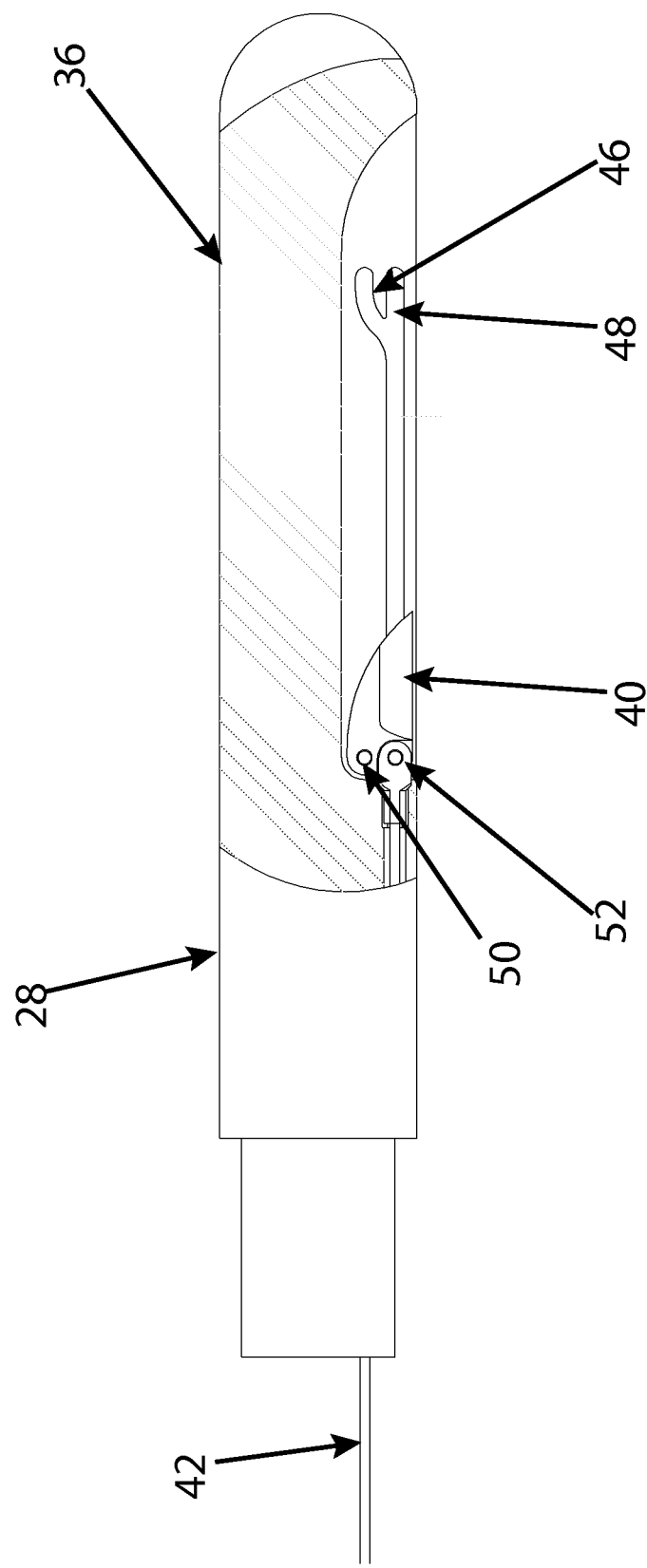

As the blade 40 is pulled toward the proximal end of the catheter 28, upper control pin 50 forces the blade 40 to rotate clockwise as seen in FIG. 3B. As shown in FIG. 3C, when upper control pin 50 has reached the lowest point in upper control slot 46, the blade 40 has fully extended. In this embodiment, the upper control slot approaches and merges with the lower control slot, although other configurations could be employed to accomplish the same result. In FIG. 3D, the blade 40 is again fully refracted, forced by control pin 52 to rotate counterclockwise.

As will be seen below the catheter can beneficially be held in place during operation by the dilation assembly. In some implementations, the dilation assembly and sliding retractable knife may be co-located in the same longitudinal section of the catheter 28. Use of a co-located sliding retractable knife and dilation assembly affords more positive control of the sliding retractable knife being held in a fixed position with respect to length and depth of cut so that the sliding retractable knife cuts a known path. It also allows continued perfusion past the dilation assembly during the procedure.

Figure 4A:
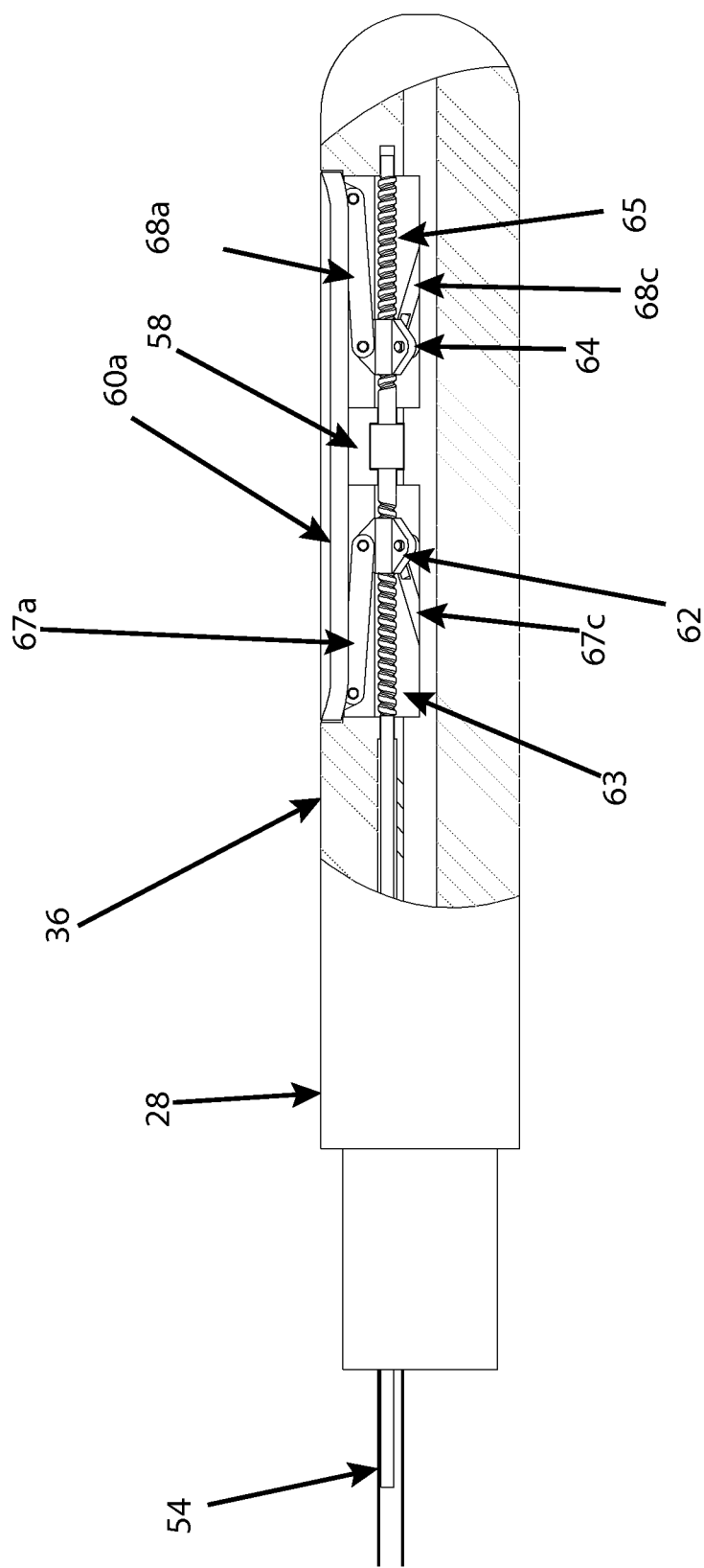
FIGS. 4A, 4B and 4C are views of a scissors jack dilation assembly.
Figure 4B:
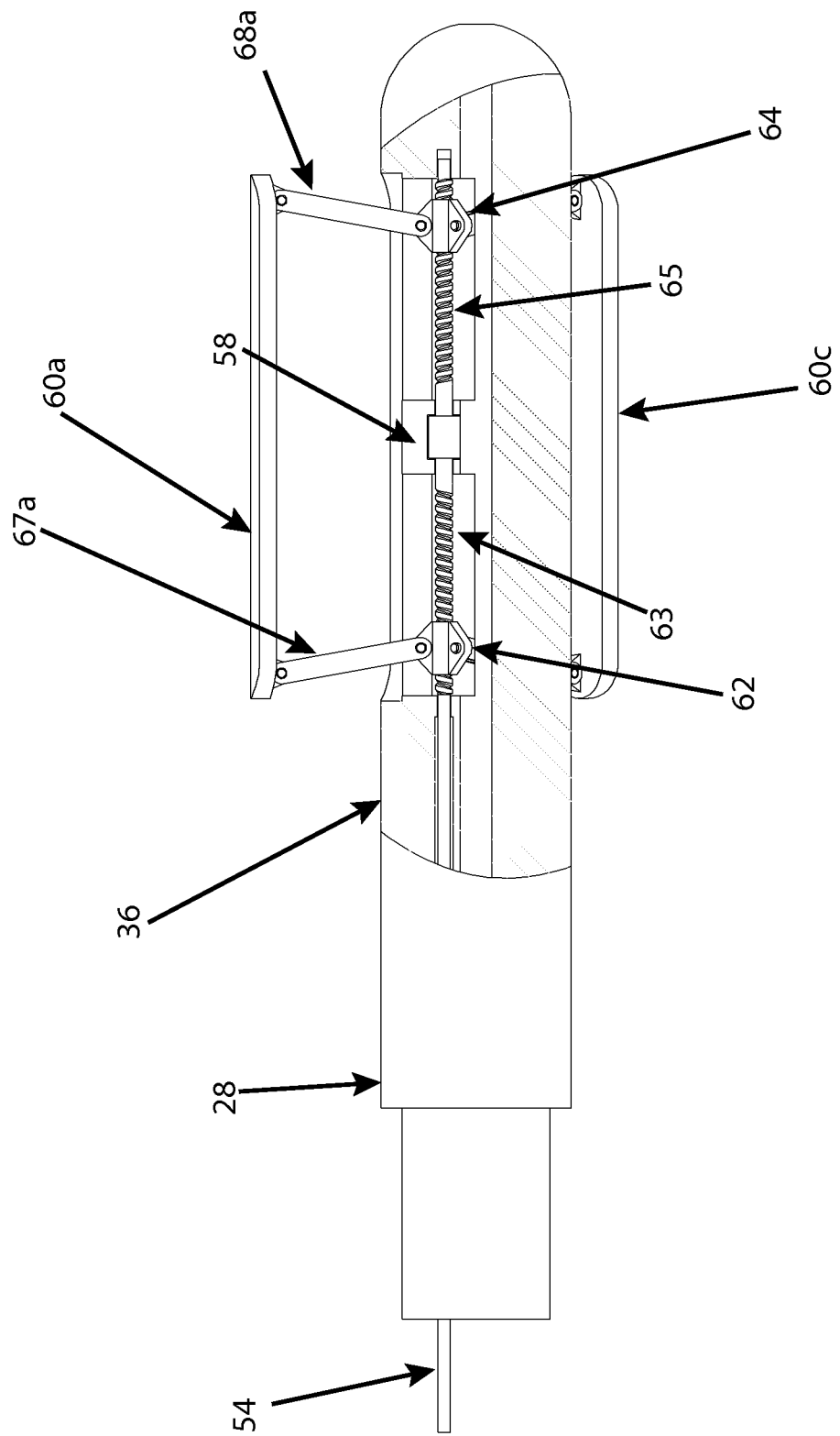
Figure 4C:
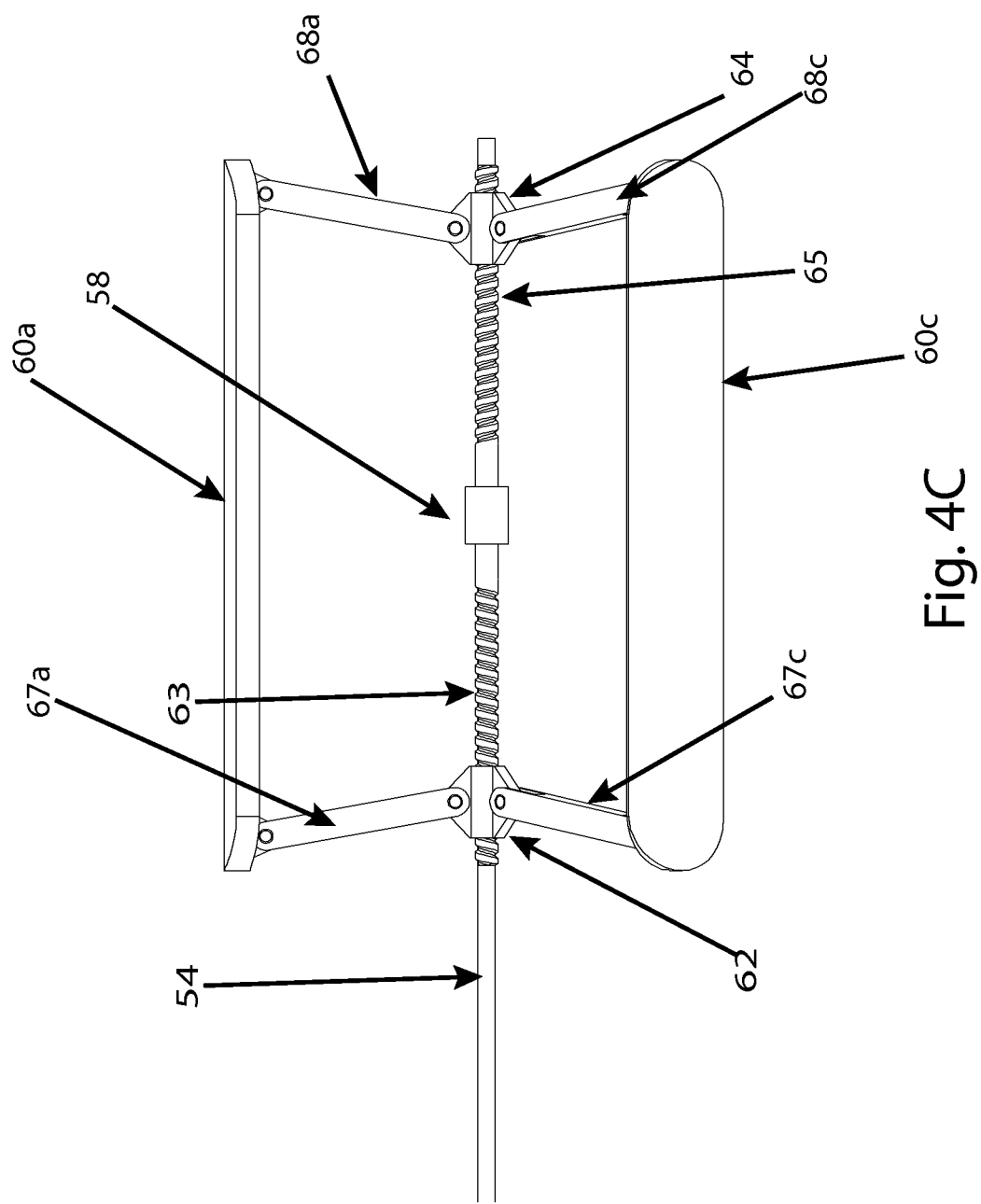

FIG. 4A shows a cutaway view of a dual lever "scissors jack" type dilation assembly in the closed position. The embodiment shown has three extendable panels 60 (of which only one 60a is visible in FIG. 5A) although fewer or more panels could be used for the present invention. In this embodiment of the scissors jack, a stationary member 58 rotatably contains the control rod 54 in a captured fashion such that the control rod 54 may rotate freely but not move proximally or distally with respect to the catheter 28. The control rod 54 comprises a proximal portion 63 and a distal portion 65, which are respectively threaded in opposite manners. In consequence, nuts 62 and 64 move along the control rod 54 in opposite directions when the control rod 54 is rotated. Expandable panel 60a is attached hingedly to lever arms 67a and 68a which in turn are attached hingedly to nuts 62 and 64 respectively, such that as nuts 62 and 64 move apart, lever arms 67a and 68a extend causing expandable panel 60a to move outwardly from the surface of the catheter 28. Expandable panels 60b and 60c (not seen in this view) are similarly attached to levers 67b, 68b, 67c and 68c respectively which are in turn hingedly attached to nuts 62 and 64. As shown in FIG. 4B, control rod 54 has been turned causing nuts 62 and 64 to move away from one another and causing levers 67a and 68a to extend, thereby causing the expandable panel 60a to extend from the side of the catheter 28. In this view only two expandable panels 60a and 60b are visible and only two levers 67a, and 68a are shown. FIG. 4C shows only the scissors jack mechanism without the surrounding structure for greater clarity. In this view two expandable panels 60a and 60c can be seen clearly, as well as two sets of levers 67a, 67c 68a and 68c. Other implementations of a scissors jack to perform the same function well-known in the art could be used beneficially.

The dilating assembly may be co-located with the sliding retractable knife or placed elsewhere over the length of the catheter 28 and used sequentially with the sliding adjustable knife by first dilating the stenosis and then performing the incision. It is beneficial, however, to co-locate the dilation assembly with the sliding retractable knife as it serves to hold the sliding retractable knife in position over the myocardium to be incised.

FIG. 5C shows another embodiment of the scissors jack means wherein the side portions brace 58 is movable. Either through a slot in the side of the catheter (not shown) or by replacing a portion of the side of the catheter with the member 58, member 58 can hold the catheter in position against the wall of the artery (not shown).

Figure 5A:
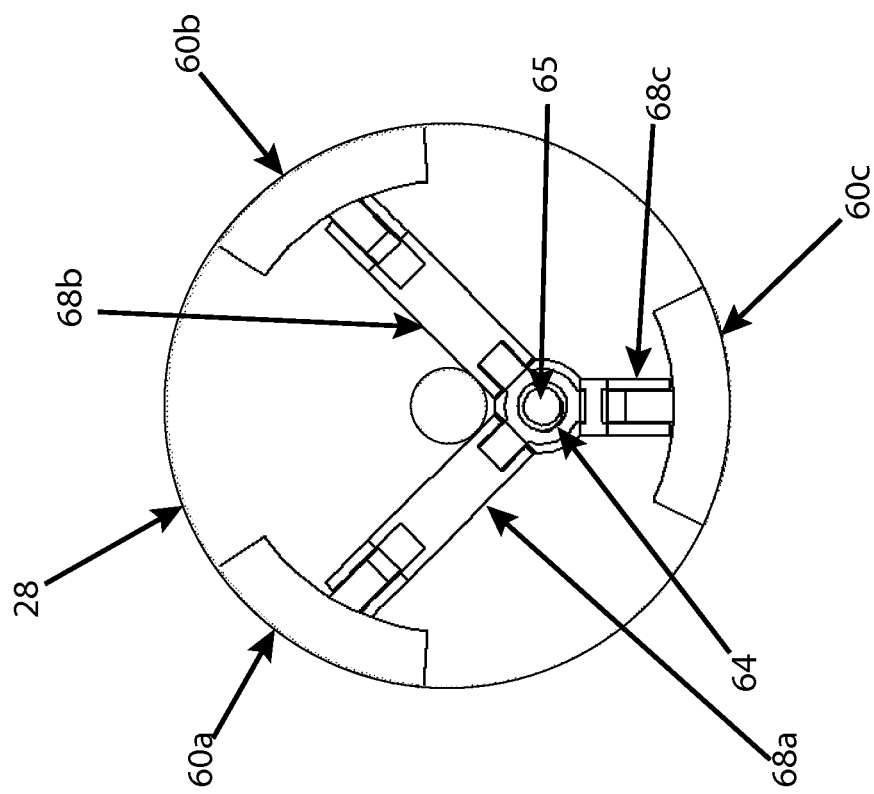
FIG. 5A is a view of a cutaway end view of a scissors jack dilation assembly in the closed position.
Figure 5B:
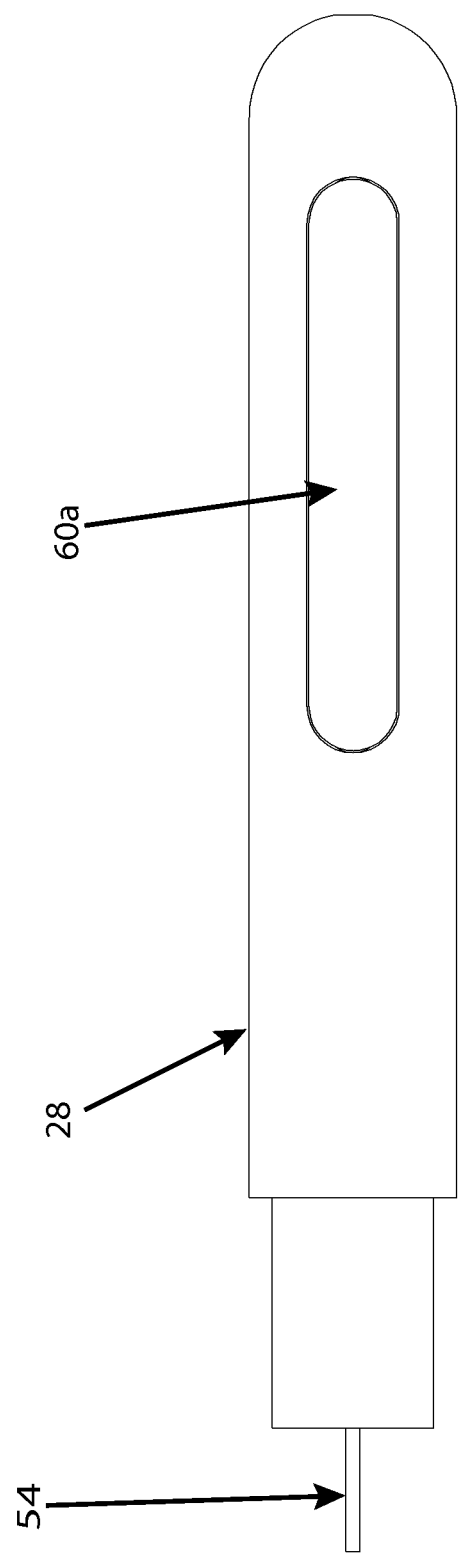
FIG. 5B is a side view of the distal end of the catheter showing one of the expanding panels of the dilation assembly in the closed position.
Figure 6:
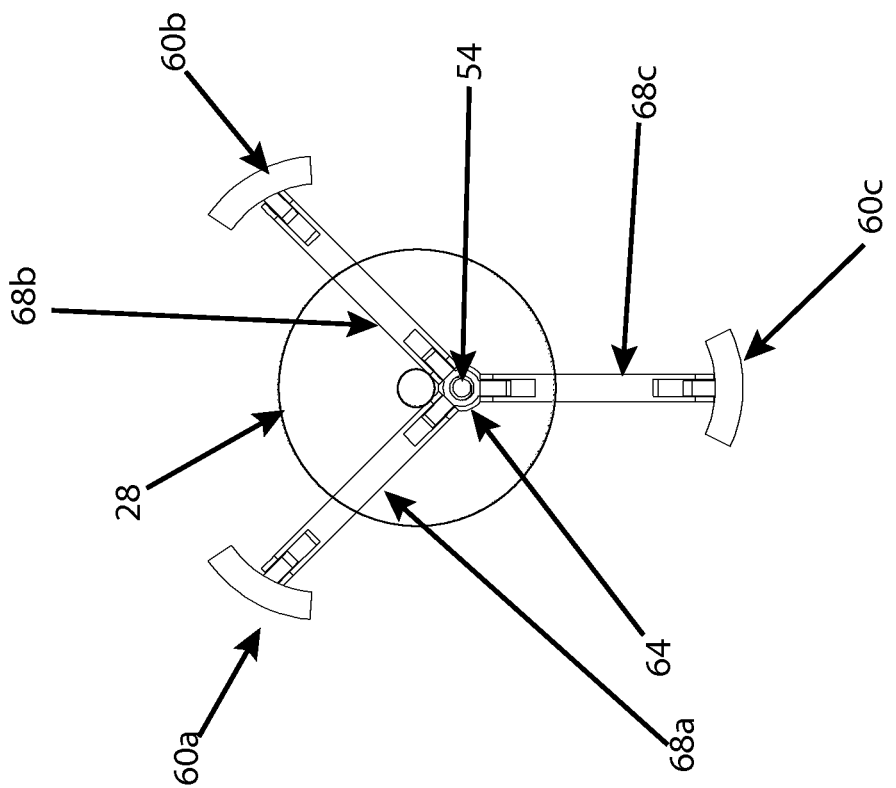
FIG. 6 is a view of a cutaway end view of a scissors jack dilation assembly in the open position.

A cutaway cross section view of the catheter at the dilating assembly looking from the distal end of the catheter 28 is shown in FIG. 5A. This view shows a dilation assembly with three expandable panels 60a, 60b and 60c. Fewer or greater expandable panels may be implemented within the scope of the present invention. The expandable panels 60a, 60b and 60c are shown in refracted position. Three levers 68a, 68b and 68c can be seen (levers 67a, 67b and 67c are not visible in this view) hingedly attached to the expanding panels 60a, 60b and 60c respectively and to nut 64 riding on the distal portion 65 of control rod 54 (visible in cross-section). FIG. 5B shows a view of the distal end of catheter 28 a showing an expandable panel 60a in the closed position. Other expandable panels 60b and 60c are not visible from this view. Referring to FIG. 6, the same view is given as in FIG. 5A only in this view the expandable panels 60a, 60b and 60c are shown in the extended position. When extended, expandable panels 60a, 60b and 60c dilate the stenosis. This method of dilation supports simultaneous perfusion during dilation, which can continue during incision.

Referring to FIG. 8A, a cutaway view of a spiral knife cutting means is shown. A blade (not shown) is attached to a flexible but stiff membrane 75, which is wound around a control rod (not shown) attached to a controller 34 at the proximal end of the catheter 28. A guide 78 is provided to guide the blade and the stiff membrane 75 when in use. The material from which the stiff membrane 75 is made may be such as to have memory which causes it to straighten when not on around the control rod. FIG. 8B shows the same spiral knife cutting means with the blade 76 extended. Controller 34 has been rotated in the direction 35. FIG. 8C is a transected view perpendicular to the longitudinal axis of catheter 28. The spiral of the flexible membrane 75 is wrapped around the hollow control rod 33, through which guide wire 32 runs. Just as easily, guide wire 32 could run outside and parallel to control rod 33.

An RF cutting wire means is shown in FIGS. 9A, 9B, 9C and 9D, shown in sequential steps of operation. An RF cutting wire is well known in the art, being basically a wire carrying an radio frequency signal the emission of which from the end region of the wire cuts the tissue. An RF cutting wire 86 is contained within a guide 92, being a hollow tube. The end of the RF cutting wire 86 is shown retracted above in a cutaway view of a portion of the catheter 28. A slot (not shown) within which they RF cutting wire 86 can extend and travel permits the RF cutting wire 86 when extended to protrude beyond the outer perimeter of the catheter 28. A spacer 88 is placed between the proximal end of the guide 92 and a stop 90 attached to the proximal end of the RF cutting wire 84. With the spacer 88 in place, the stop 90 pressing against the spacer 88 effectively prevents the RF cutting wire 86 from protruding beyond the outer perimeter of the catheter 28.

Figure 9A:
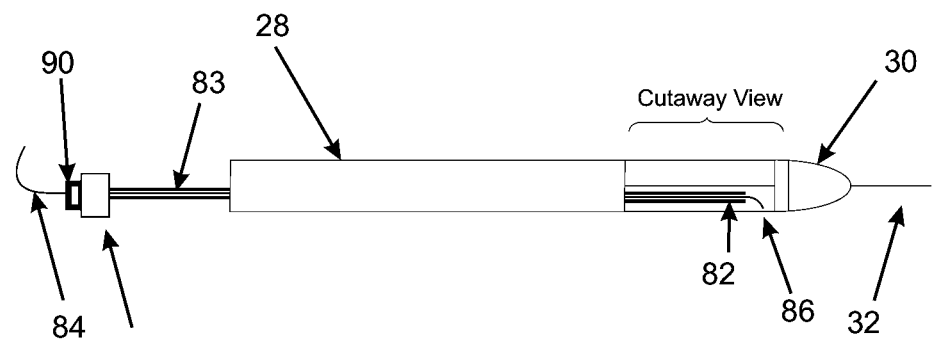
FIGS. 9A, 9B, 9C and 9D are views of an RF wire cutting means being deployed and retracted, in sequence.
Figure 9B:
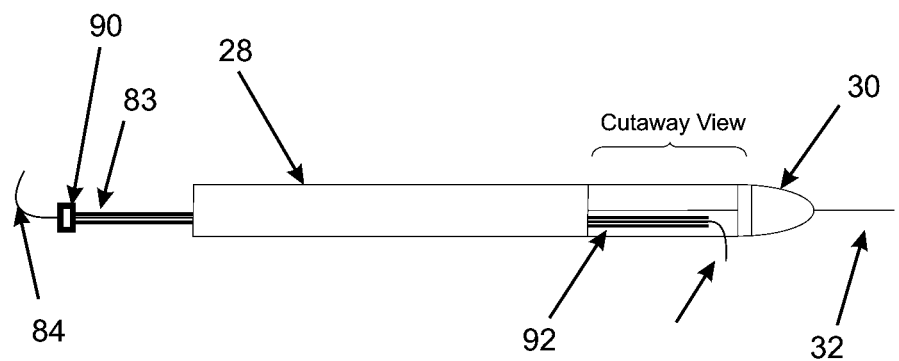

FIG. 9B shows the same RF cutting wire cutting means with the spacer 88 removed. The stop 90 has been moved proximate the proximal end of the guide tube 92, thus allowing the stop 90 and RF cutting wire to move toward the distal and of the catheter the distance of the spacer 88, plus enable in the RF cutting wire 86 to extend beyond the outer perimeter of the catheter 28.

Figure 9C:
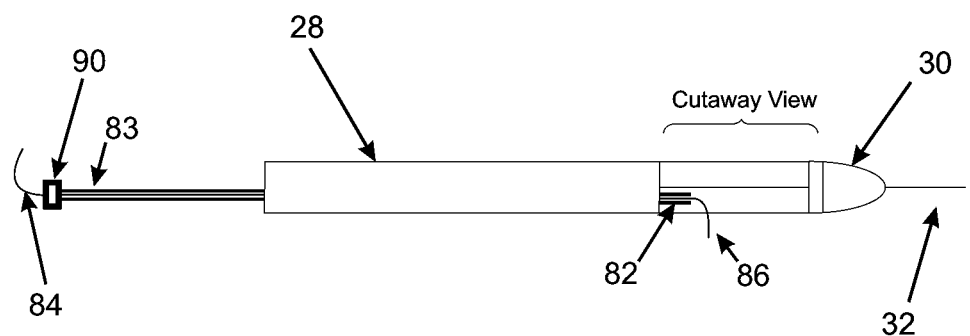
Figure 9D:
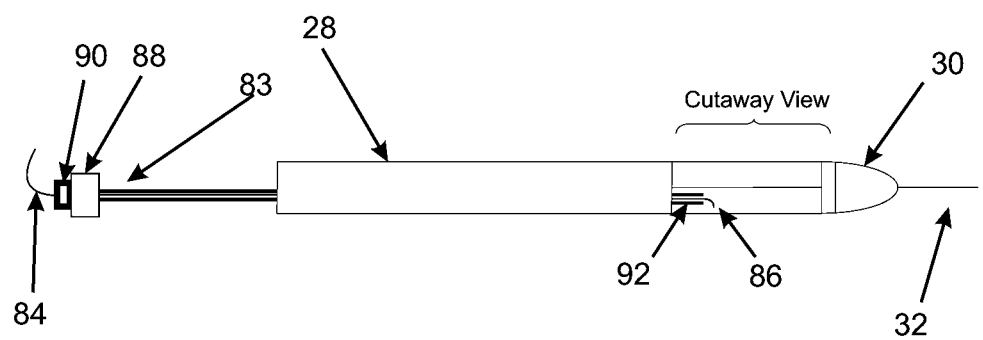

Referring to FIG. 9C, the guide 82 has been shifted away from the proximal end of the catheter 28 the distance of the desired cut. In FIG. 9D, the spacer 88 is then reinserted, thus moving the proximal end of the RF wire 84 and stop 90 a sufficient distance from the proximal end of the guide 92 to cause the RF wire 86 to withdraw inside the perimeter of the catheter 28. A slot (not shown) in the bottom of the catheter exists to permit the RF wire to extend beyond the perimeter of the catheter 28 for purposes of performing the cut. The depth of the cut can be set by the size of the spacer 88.

A robotic movement and rotation device may be utilized to control the motion of the catheter 28 or RF cutting wire 86 or both. The stop, 90 can be in the form of an adjustable stop, allowing a variable depth of cut, and too, can be controlled robotically. Previously recorded data from and intravascular ultrasound or other sensing means which contours the interior of the artery may be used to control the robotic movement and rotation device to cut a curve in the artery and myocardium, thus not limiting the cut to a straight line or a fixed depth.

Alignment of the cutting means is important. In order to create the new desired vessel geometry, the cutting means may need to cut through the vessel wall and in the case of a coronary artery, into the supporting myocardium. Therefore, it is important to position the cutting means so it cuts into the myocardium and not into the pericardium, or said another way, into the heart instead of away from the heart. Alignment can be accomplished by several means. As described by Lary in U.S. Pat. No. 5,713,913 "Device and method for transecting the coronary artery," a radiographic means could be used. However due to the resolution of the x-ray systems and the fact that the heart is beating there may be difficulty in assessing the proper alignment of the cutting means as described by Lary. More effective means for positioning the cutting means in the orientation that would cut into the heart is desirable.

Figure 7:
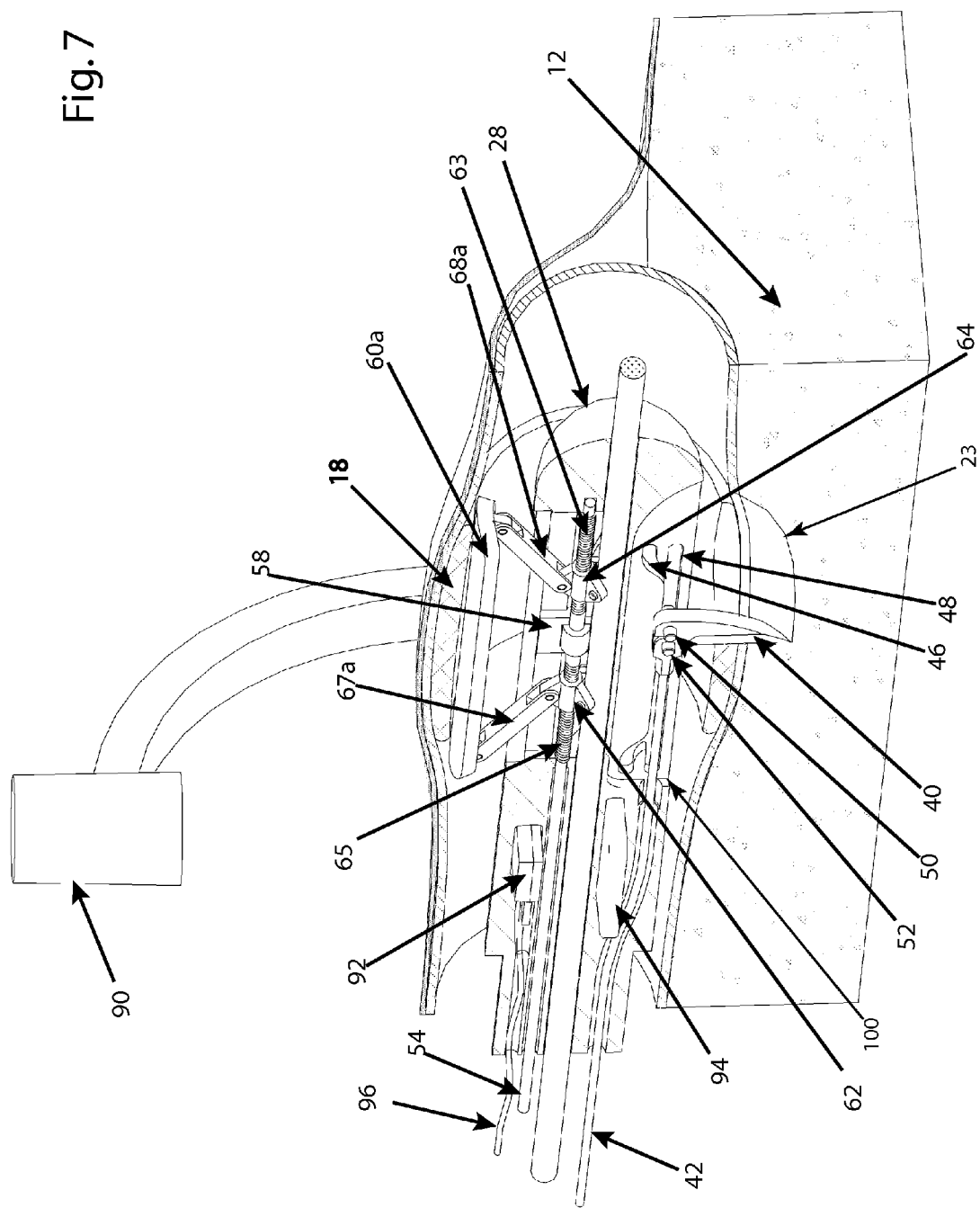
FIG. 7 are views of a spiral cutting means in the closed and open positions is a cutaway view showing a scissors jack dilation assembly collocated with a sliding retractable knife as well as an x-ray sensor and x-ray blocker and a stylized x-ray source.

FIG. 7 shows a cutaway view of the distal end of catheter 28 showing the collocated sliding retractable knife and expandable panel dilating assembly together with an x-ray positioning assembly. The internal parts of the x-ray positioning assembly comprise an x-ray sensor 92 and an x-ray blocker 94. The x-ray sensor 92 is placed so as to be in a known orientation and position with respect to the sliding retractable knife 40. As shown, the x-ray sensor is on the opposite side from the sliding retractable knife 40. An external x-ray source 90 will produce maximal signal in the x-ray sensor 92 when the x-ray blocker 94 is not blocking the signal from the x-ray source 90 to the x-ray sensor 92 when in the desired orientation. The shape of the x-ray blocker 94 need not be flat or rectangular, but may be any beneficial shape such as curved to match the shape of the catheter and thus more precisely define the unblocked area. Thus, the sliding retractable knife blade 40 may be positioned toward the myocardium 12 at the stenosis 18. The x-ray sensor 92 signal may be conveyed externally by means of one or more wires 96 running from the x-ray sensor to and extending from the proximal end of the catheter to suitable receiving equipment to display the signal strength received by the x-ray sensor 92.

For example, one could use an x-ray sensor on the catheter and an x-ray blocker in known orientation and position with respect to the cutting means such that the sensor would indicate the optimal position of the catheter to cut into the heart based upon the position of the x-ray emitter commonly used in the catheter lab to perform cine.

Another means of alignment is to position a magnet on the catheter with one pole pointed in the proper orientation and the other end treated to optimize the field in conjunction with a magnetic sensor located outside the chest will allow proper positioning of the catheter and attached cutting means. Alternatively, the magnetic field can be applied from outside the body, and a sensor such as a Hall effect switch or fluxgate chip which is attached to one or more wires running the length of the catheter from the distal to the proximal end. Shielding of the internal sensor may be used to inhibit triggering when the catheter is not in the optimal position.

Figure 8:
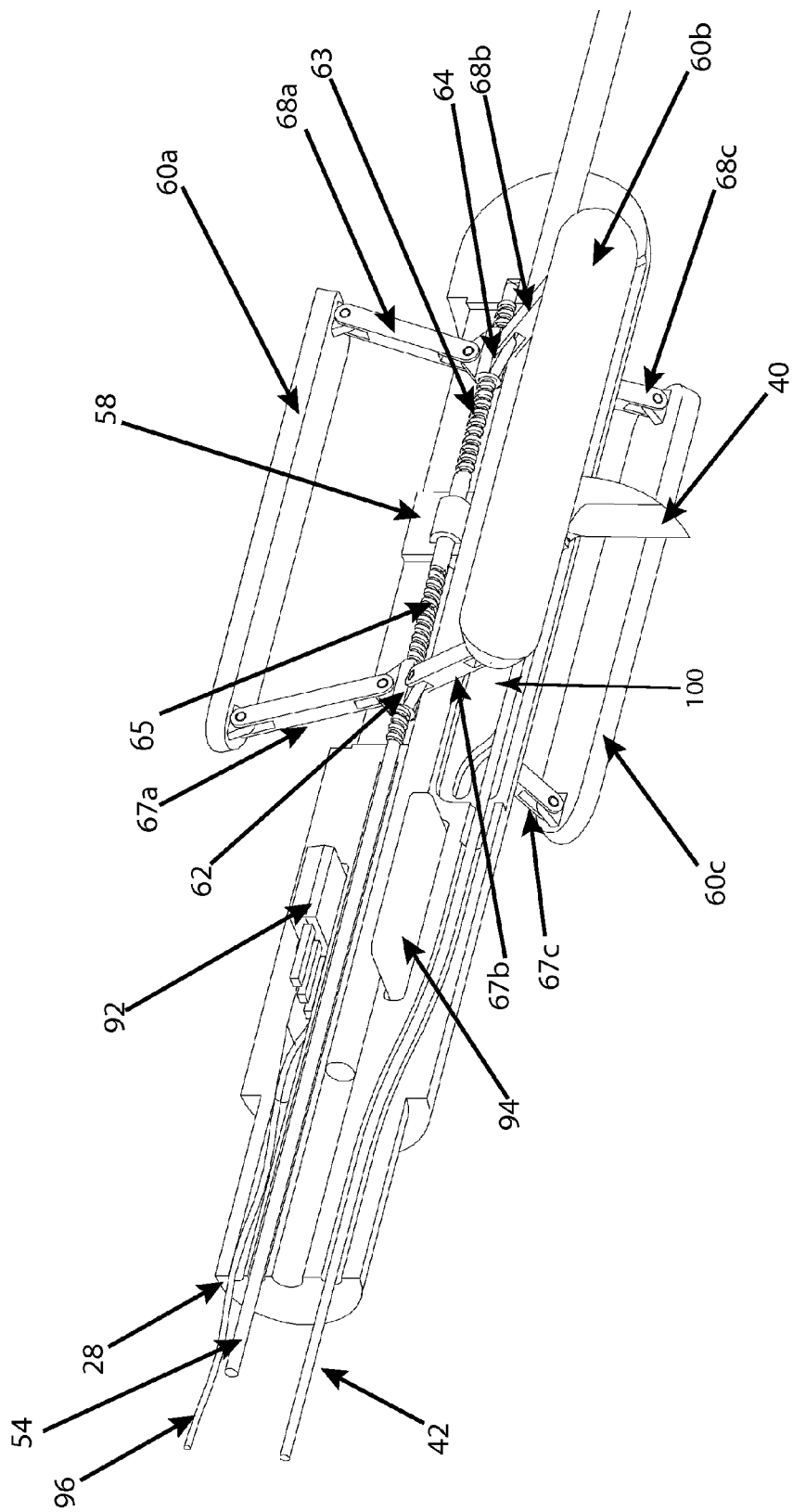
FIG. 8 shows another cutaway view of a siding retractable knife and scissors jack dilation assembly with three expandable panels visible co-located in the distal end of a catheter, with x-ray-blocker and x-ray sensor positioning assembly.

Another means of alignment is to position an antenna on the catheter with one side collecting an emitted signal from outside the chest and the other treated in such a means as to indicate which side is facing the outside of the body, or away from the heart. Again, shielding may be used to inhibit signal reception when the catheter is not in optimal position, FIG. 8 shows yet another cutaway view of the distal end of the catheter with all expandable three panels 60a, 60b and 60c visible as well as their respective lever arms 67a, 67b, 67c, 68a, 68b and 68c.

Another means of alignment is to provide a light sensor on the catheter which can sense a light source that passes through the body from outside the body and therefore indicate the relationship between the sensor and emitter. Knowing the relationship between the sensor and the cutting means enables positioning the cutting means. If the sensor is placed on the catheter away opposite the cutting means, a peak signal indicates the cutting means is placed toward the heart. The sensor can be shielding to inhibit light reception an all but the optimal position of the catheter, that is, when the cutting means is proximate the heart.

Another means comprises utilizing the natural electrical signals from the heart muscles contracting as the alignment method. It is well published that the heart muscles emit electrical signals on a regular basis and these signals are currently used to map the heart for ischemic sections, those with little or no signal. The present invention can utilize a directional receiver such that when the receiver was positioned to receive the maximum signal it would be facing normal to the heart and into the heart, enabling positioning the cutting means by knowing the positional relationship between the sensor and the cutting means.

The details of one or more embodiments of the invention are set forth in the accompanying drawings and the description below. Other features and advantages of the invention will become apparent from the description, the drawings, and the claims.

The invention has been described in terms of particular embodiments. Other embodiments are within the scope of the following claims. For example, the steps of the invention can be performed in a different order and still achieve desirable results. Modifications and substitutions by one of ordinary skill in the art are considered to be within the scope of the present invention, which is not to be limited except by the following claims.

The invention claimed is:

1. A device for treating a coronary stenosis comprising:
a catheter having a distal end and a proximal end and a longitudinal axis and an inner surface and an outer surface;
further comprising a sliding retractable knife assembly located in said distal end comprising:
a knife blade comprising a sharpened edge, a top edge, a lower control pin and an upper control pin, both said upper and lower control pins mounted and protruding through said knife blade proximate to and in line substantially parallel to said top edge, said lower pin being proximate to said sharpened edge;
further comprising a knife slot through said catheter running parallel with said longitudinal axis, said knife slot being sized so that said knife blade may pass closely edgewise within said knife slot;
further comprising a first rail and a second rail each approximately equal in length to said knife slot, said rails fixedly mounted one on either side of said knife slot; said rails each having an inner side facing said knife slot; said first and second track rail inner sides each further comprising an upper pin slot and a lower pin slot; all the said pin slots running substantially parallel to said longitudinal axis and adapted to slidably receive said first and second pins;
said knife blade having a first retracted position with said sharpened edge proximate to and parallel to said knife slot and said knife blade being disposed between said first and second track rails with said upper control pin engaged within said first and second upper pin slots respectively and said lower control pin engaged within said first and second lower pin slots respectively;
said knife blade further comprising a control wire rotatably attached to said lower control pin, said wire running from said lower control pin through said catheter to said proximate end of said catheter, operable by pulling on said lower control pin toward said the proximal end to cause movement of said knife blade in the proximal direction, and said upper control pin sliding thereby in said upper pin slots operable to cause said knife blade to rotate so as to position said sharpened edge outwardly through said knife slot approximately normal to said outer surface, with continued movement in the proximal direction and continued pulling on said control pin causes said knife blade to move the length of the knife slot wherein said upper control pin moving in said upper control slots is operable to rotate said knife blade into a second retracted position similar to said first retracted position.

2. The device in claim 1 further having expandable sides dilation means with said sliding retractable knife co-located with said expanding sides dilation means along said longitudinal axis within said catheter.

3. The device in claim 1 further comprising an alignment assembly, said alignment assembly comprising: an x-ray sensor and an x-ray blocker;
said x-ray sensor being mounted away from and in predetermined alignment with said retractable knife, and further comprising at least one signal wire connected to said x-ray sensor and running through said catheter to said proximate end, operable to convey an x-ray sensing signal;
said x-ray blocker being mounted proximate to said inner surface and co-located along said longitudinal axis with said x-ray sensor blocking x-ray penetration thereby on all but a portion of said inner surface in the region of said x-ray sensor.

* * * * *

UNITED STATES PATENT AND TRADEMARK OFFICE
CERTIFICATE OF CORRECTION

| | | |
|---|---|---|
| PATENT NO. | : 8,551,129 B2 | Page 1 of 2 |
| APPLICATION NO. | : 12/270889 | |
| DATED | : October 8, 2013 | |
| INVENTOR(S) | : Lary et al. | |

It is certified that error appears in the above-identified patent and that said Letters Patent is hereby corrected as shown below:

In the Drawings;
Drawing Sheet 10, Fig. 4C, the reference numeral '60c', should read -60b-

Drawing Sheet 14, Fig. 7, the reference number '12', should read -10-

Drawing Sheet 16, Figs. 9A and 9B should be deleted in their entirety

Drawing Sheet 17, Figs. 9C and 9D should be deleted in their entirety

Figure 10:
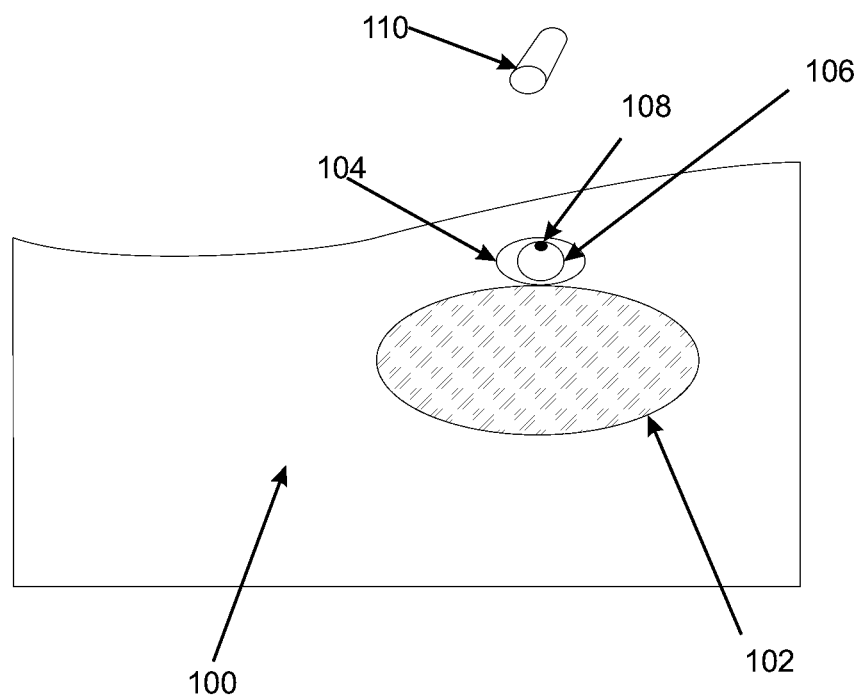
FIG. 10 is a schematic diagram showing arrangement of a variety of positioning means.

Drawing Sheet 18, Fig. 10 should be deleted in its entirety

In the Specification;
Column 3, lines 42-67 should be deleted

Column 4, line 34 "are views of a spiral cutting means in the closed and open positions" should be deleted Column 4, lines 43-46 should be deleted Column 4, line 63, 'the=rough' should read -through- Column 5, lines 13-18 should be deleted Column 5, line 62, 'Fig. 5A' should read -Fig. 4A-

Column 6, line 17, the reference number '60b', should read -60c-

Column 6, line 20, the reference number '60c', should read -60b-

Signed and Sealed this
Eighteenth Day of February, 2014

Michelle K. Lee
*Deputy Director of the United States Patent and Trademark Office*

CERTIFICATE OF CORRECTION (continued)
U.S. Pat. No. 8,551,129 B2

Column 6, lines 33-38 should be deleted

Column 6, lines 59-67 should be deleted

Column 7, lines 1-49 should be deleted

Column 8, line 14, the reference number '12', should read -10-

Column 8, lines 27-44 should be deleted

Column 8, lines 49-67 should be deleted

Column 9, lines 1-8 should be deleted